(12) United States Patent
Gu et al.

(10) Patent No.: US 9,555,003 B2
(45) Date of Patent: Jan. 31, 2017

(54) ORAL SOLID FORMULATION OF COMPOUND ANTI-TUBERCULAR DRUG AND PREPARATION METHOD THEREOF

(75) Inventors: Maojian Gu, Pudong District (CN); Qilan Zheng, Shanghai (CN); Chao Xu, Fuyang Hangzhou (CN); Ning Li, Fuyang Hangzhou (CN); Guixian Chen, Fuyang Hangzhou (CN); Lan Zheng, Fuyang Hangzhou (CN); Min Wang, Fuyang Hangzhou (CN); Lintao Jiang, Fuyang Hangzhou (CN)

(73) Assignee: Zhejiang Hisun Pharmaceutical Co., Ltd., Jiaojang District, Taizhou, Zhejiang (CN)

( * ) Notice: Subject to any disclaimer, the term of this patent is extended or adjusted under 35 U.S.C. 154(b) by 125 days.

(21) Appl. No.: 14/111,323

(22) PCT Filed: Apr. 10, 2012

(86) PCT No.: PCT/CN2012/073689
§ 371 (c)(1),
(2), (4) Date: Dec. 17, 2013

(87) PCT Pub. No.: WO2012/139485
PCT Pub. Date: Oct. 18, 2012

(65) Prior Publication Data
US 2014/0127294 A1     May 8, 2014

(30) Foreign Application Priority Data
Apr. 12, 2011 (CN) .......................... 2011 1 0091596

(51) Int. Cl.
*A61K 9/28* (2006.01)
*A61K 31/133* (2006.01)
(Continued)

(52) U.S. Cl.
CPC ............... *A61K 9/286* (2013.01); *A61K 9/209* (2013.01); *A61K 9/2086* (2013.01); *A61K 9/28* (2013.01);
(Continued)

(58) Field of Classification Search
CPC ........ A61K 9/286; A61K 9/2086; A61K 9/28; A61K 9/2866; A61K 9/209; A61K 9/284; A61K 9/2885; A61K 31/4409; A61K 31/496; A61K 31/133; A61K 31/4965
(Continued)

(56) References Cited

U.S. PATENT DOCUMENTS

| 4,681,765 A | * | 7/1987 | Guley | .................. A61K 9/4841 424/455 |
| 2003/0072800 A1 | * | 4/2003 | Singh | ..................... A61K 9/209 424/464 |

FOREIGN PATENT DOCUMENTS

| CN | 1388758 A | 1/2003 |
| CN | 1408354 A | 4/2003 |

(Continued)

OTHER PUBLICATIONS

Int'l Search Report issued Jul. 12, 2012 in Int'l Application No. PCT/CN2012/073689.
(Continued)

*Primary Examiner* — Ernst V Arnold
*Assistant Examiner* — Hong Yu
(74) *Attorney, Agent, or Firm* — Panitch Schwarze Belisario & Nadel LLP

(57) ABSTRACT

Provided is an oral solid preparation of a compound anti-tubercular drug, wherein the active ingredients are rifampicin, isoniazid, pyrazinamide and ethambutol hydrochloride. The compound oral solid preparation is a coated tablet with coated core or a coated three-layer tablet, wherein the two
(Continued)

The HPLC chromatogram measuring the related substances of the rifampicin solid dispersions (sample according to Example 7) prepared by hot melting method on day 0 active ingredients rifampicin and isoniazid do not come to contact with each other directly. The compound oral solid preparation not only improves the stability of the compound preparation, but also improves the bioavailability of rifampicin.

8 Claims, 6 Drawing Sheets

(51) Int. Cl.
*A61K 31/4965* (2006.01)
*A61K 31/496* (2006.01)
*A61K 31/4409* (2006.01)
*A61K 9/20* (2006.01)
*A61K 9/24* (2006.01)

(52) U.S. Cl.
CPC ............. *A61K 9/284* (2013.01); *A61K 9/2866* (2013.01); *A61K 9/2886* (2013.01); *A61K 31/133* (2013.01); *A61K 31/4409* (2013.01); *A61K 31/496* (2013.01); *A61K 31/4965* (2013.01)

(58) Field of Classification Search
USPC ... 424/465, 474, 479, 480; 514/254.11, 354, 514/255, 669
See application file for complete search history.

(56) References Cited

FOREIGN PATENT DOCUMENTS

| | | |
|---|---|---|
| CN | 1602872 A | 4/2005 |
| CN | 101524355 A | 9/2009 |
| WO | 2002011728 A2 | 2/2002 |
| WO | WO 02/087547 * 11/2002 | ............... A61K 9/20 |

OTHER PUBLICATIONS

Singh et al, "The Reason for an Increase in Decomposition of Rifampicin in the Presence of Isoniazid under Acid Conditions," Pharm. Pharmacol. Commun., vol. 6, pp. 405-410 (2000).

Sosa et al, "Rifampicina and bioavailability in combination formulation," Ars. Pharm., vol. 46, No. 4, pp. 353-364 (2005).

* cited by examiner

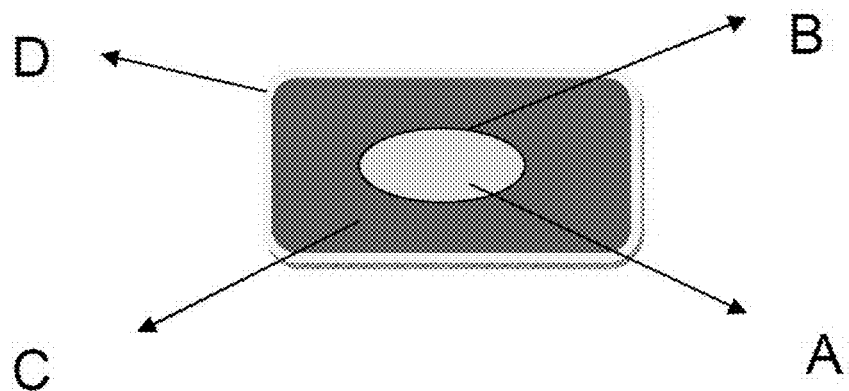
Fig.1 A coated tablet with coated core
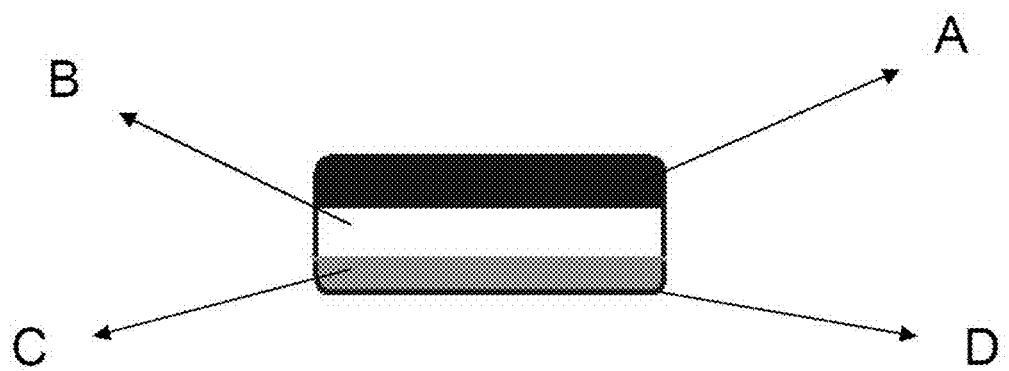
Fig.2 A three-layer coated tablet

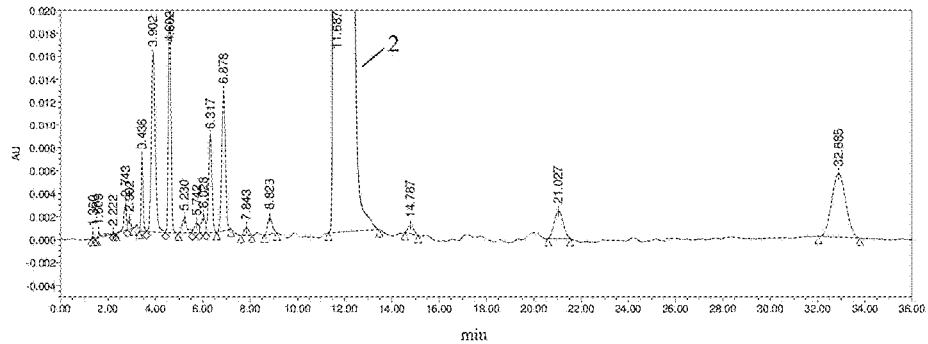
Fig. 3 HPLC chromatogram measuring the related substances of the rifampicin bulk drug of batch No. 0811011 on day 0
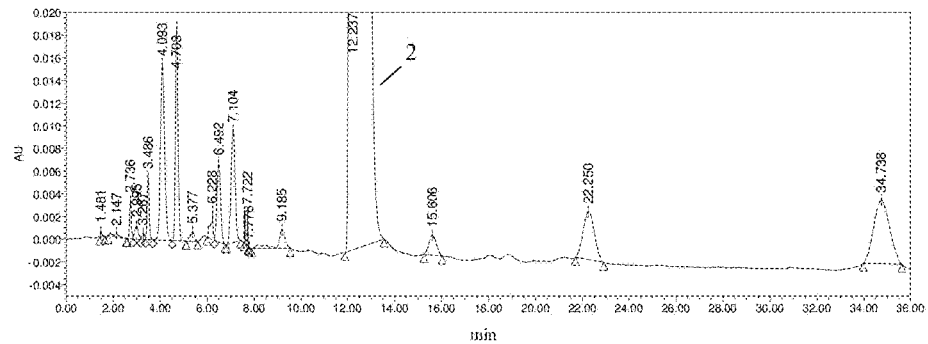
Fig. 4 The HPLC chromatogram measuring the related substances of the rifampicin solid dispersions (sample according to Example 8) prepared by spray drying method on day 0

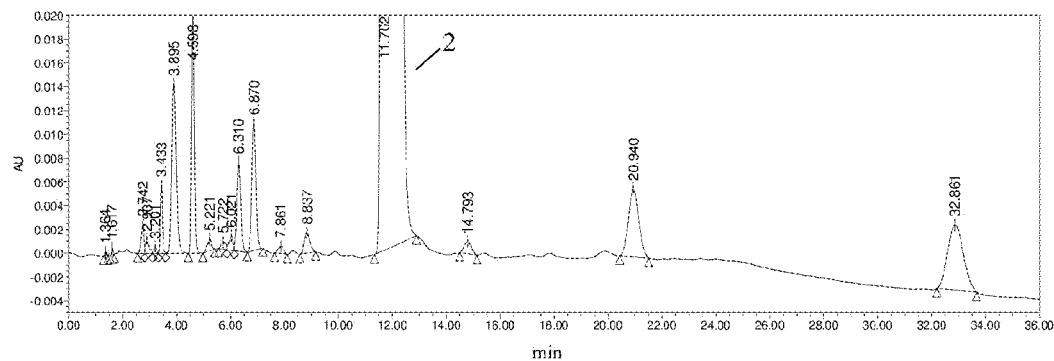
Fig.5 The HPLC chromatogram measuring the related substances of the rifampicin solid dispersions (sample according to Example 11) prepared by solvent spontaneous evaporation method on day 0
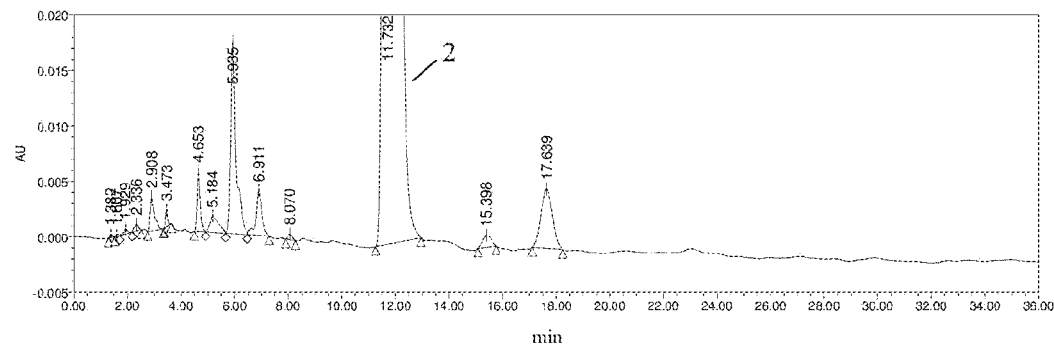
Fig.6 The HPLC chromatogram measuring the related substances of the rifampicin solid dispersions (sample according to Example 7) prepared by hot melting method on day 0

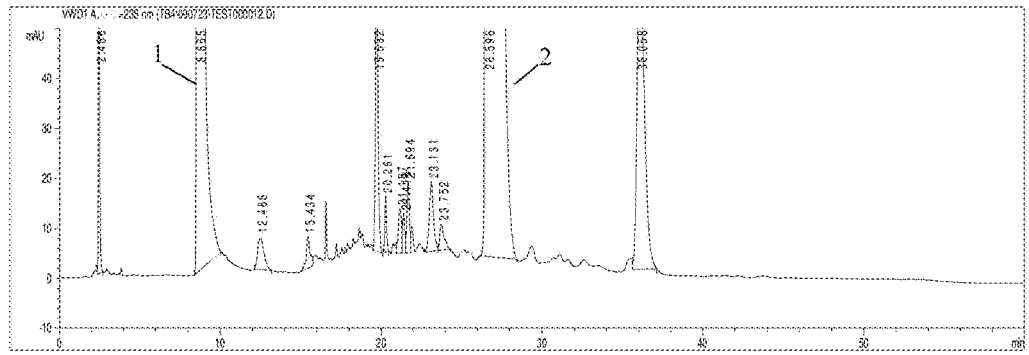
Fig.7 HPLC chromatogram measuring the related substances of an imported product after accelerated experiment (40°C, 75%RH) for 6 months
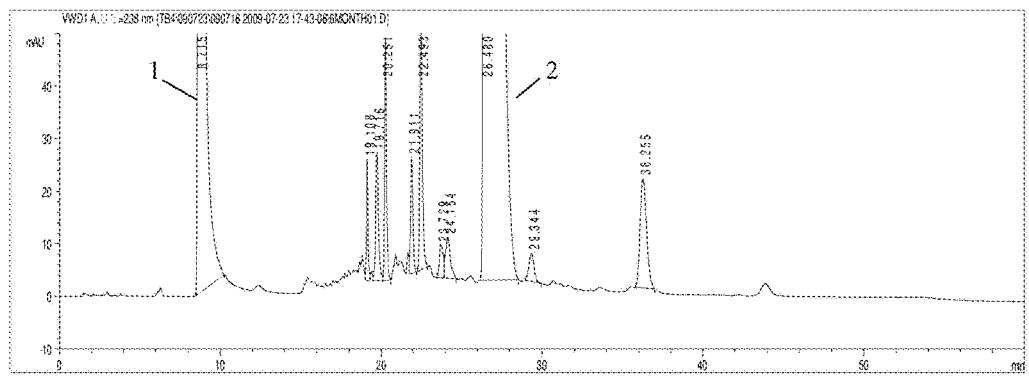
Fig.8 The HPLC chromatogram measuring the related substances of the inventive coated tablet with coated core after accelerated experiment (40°C, 75%RH) for 6 months

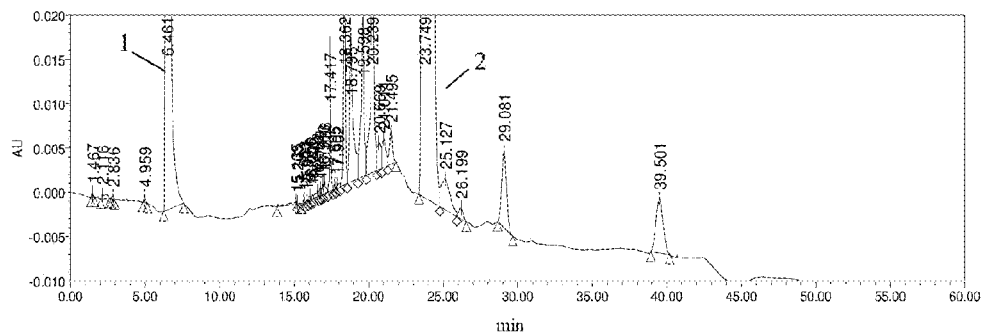
Fig.9 HPLC chromatogram measuring the related substances of the inventive coated tablet with coated core after accelerated experiment (25°C, 60%RH) for 12 months
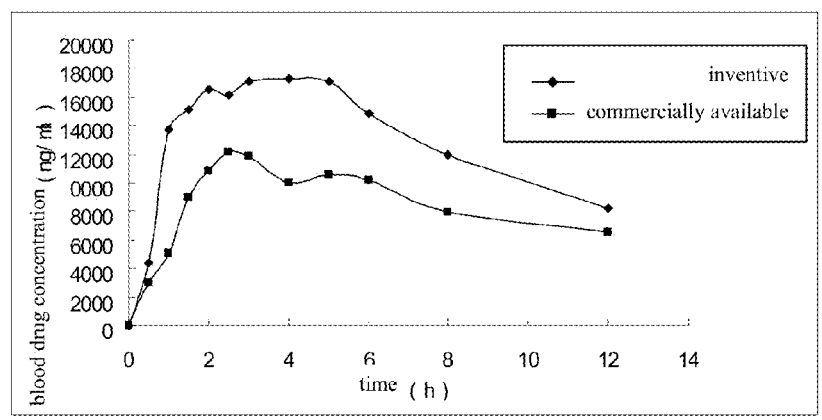
Fig.10 The profiles of time vs. drug blood level after singly administrating beagles with the inventive rifampicin (sample in Example 11) and commercially available rifampicins

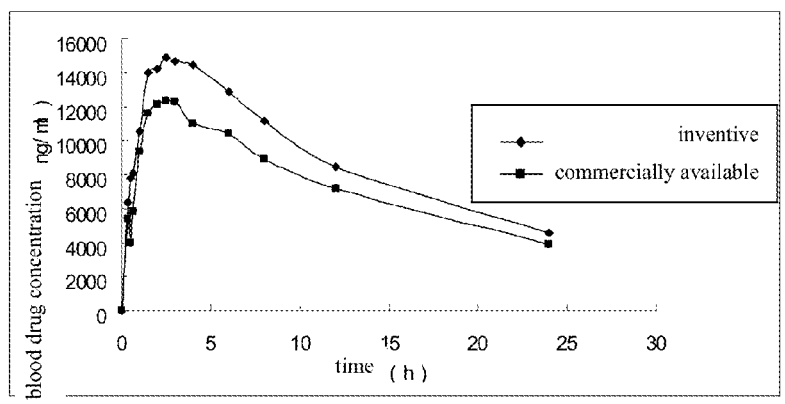
Fig.11 The profiles of time vs. drug blood level after administrating beagle with the inventive rifampicin + commercially available isoniazid and commercially available rifampicin + commercially available isoniazid

ORAL SOLID FORMULATION OF COMPOUND ANTI-TUBERCULAR DRUG AND PREPARATION METHOD THEREOF

CROSS-REFERENCE TO RELATED APPLICATION

This application is a Section 371 of International Application No PCT/CN2012/073689, filed Apr. 10, 2012, which was published in the Chinese language on Oct. 18, 2012, under International Publication No WO 2012/139485 A1, and the disclosure of which is incorporated herein by reference.

BACKGROUND OF THE INVENTION

The present invention relates to an oral solid formulation of compound anti-tubercular drug and preparation method thereof, in particular, to an oral solid formulation of a four-ingredient compound anti-tubercular drug comprising rifampicin, isoniazid, pyrazinamide and ethambutol hydrochloride as active ingredients.

Tuberculosis is a type of chronic infectious diseases caused by tubercle *bacillus*, which may involve with various tissues and organs in the body, e.g. lung, kidney, intestine, bone etc. Among others, lung tuberculosis is the most frequently found type. Tuberculosis is a major problem influencing the health of people in developing countries. Recently emergence of *mycobacterium* infections in HIV infected individuals is also on the rise, and becomes a stubborn problem in developed countries. According to the official statistical figures published by World Health Organization (WHO), the number of diagnosis confirmed patients suffering from active tuberculosis in the world is over 20 million, while the number of newly founded patients is up to 8.7 million per year, in which the incidence of lung tuberculosis in Asia occupies 70% of total in the world. India and China occupy the first and second highest incidence of lung tuberculosis in Asia. Antibiotics are commonly used to treat tuberculosis in clinical practice. However, in contrast to treat typical bacterial infections, it requires longer time for the tuberculosis patients to be completely cured, and generally, the treatment will last for about 6-12 months. In view of the clinical treatment status, due to the long period for taking in pills, drug resistance easily generates. To some extent, the phenomenon of drug resistance is increasingly aggravating in the world mainly due to the improper treatment measures carried out, especially due to the single use of one specific kind of antibiotics, or the patient does not normally take in pills according to the prescription, such as missing doses and insufficient dosage. According to "Multidrug and extensively drug-resistant tuberculosis: 2010 global report on surveillance and response. Geneva, Switzerland: World Health Organization, 2010" which is recently finished, it is estimated that 440 thousand people in the world suffer from multidrug-resistant tuberculosis, in which one of the third have died. In view of the drug-resistant phenomenon constantly occurs, WHO and International Union against Tuberculosis and Lung Disease have both announced that it has been in the state of emergency regarding to the treatment of lung tuberculosis. Since the continuing emergence of the drug-resistant phenomenon, the fixed dose combination (FDC method) has been widely used for treating lung tuberculosis. One of the commonly used compound drugs in FDC method is a four-ingredient compound drug, i.e. in addition to the rifampicin(R) and isoniazid(H) which are most efficient for the tuberculosis treatment, it further contains pyrazinamide(Z) and ethambutol hydrochloride(E). Such a four-ingredient compound drug may be a compound drug tablet and capsule, etc, and has been formally approved and accepted by WHO for the tuberculosis treatment. Such a four-compound drug consists of a compound formulation, which increases the compliance of the patients and can reduce the occurrence of drug-resistance to some extent.

Rifampicin(R) is also known as rifampin, which is a semi-synthesized rifamycins derivative. Rifampicin is a brick red color crystal, and has a melting point of 183° C. Rifampicin is poorly soluble in water (solubility: 1.3 mg/ml in water, pH 4.3; 2.5 mg/ml in water, pH 7.3; 100 mg/ml in water, DMSO), and is unstable in acid. Rifampicin can easily react with isoniazid, and also may be oxidized by factors of air, light exposure, etc. The molecule structure of rifampicin is as below:

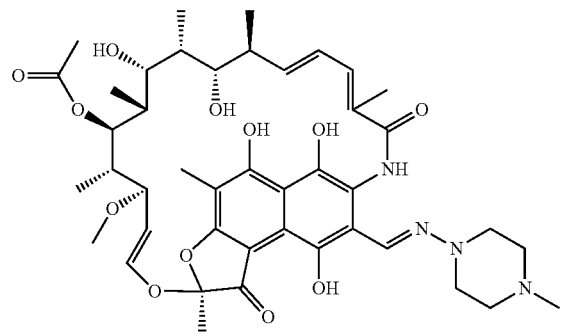 [SMILES: CO[C@@H]1/C=C/O[C@@]2(C)Oc3c(C)c(O)c4c(O)c(c(/C=N/N5CCN(C)CC5)c(O)c4c3C2=O)NC(=O)/C(C)=C/C=C/[C@H](C)[C@H](O)[C@@H](C)[C@@H](O)[C@@H](C)[C@H](OC(C)=O)[C@H]1C]

Rifampicin is an efficient broad-spectrum antibacterial drug, and has a strong effect on inhibiting or eliminating tubercle *bacillus*. The anti-tubercular effect is only slightly weaker than isoniazid, but is stronger than streptomycin. The minimum inhibitory concentration is about 0.02-0.05 μg/ml. Rifampicin has effect on the bacteria not only in the multiplication stage, but also in the rest stage. Rifampicin is also effective to the strains showing drug-resistance to other anti-tubercular drugs. Rifampicin can eliminate tubercle *bacillus* in macrophage, fibrotic cavity, caseous focus, and also have strong inhibiting effect on gram positive coccus, such as *staphylococcus aureus, streptococcus*, and pneumococcus. For gram negative coccus, such as meningococcus, gonococcus, as well as leprosy *bacillus*, rifampicin also possesses strong inhibiting effect. High concentration of rifampicin inhibits varida virus and *chlamydia trachomatis*. The single use of rifampicin tends to generate drug-resistance, and thus is usually combined with other first-line pharmaceuticals for the initial treatment and retreatment of patients suffering serious diseases, so as to enhance the efficacy and retard the generation of drug-resistance. There is no cross drug-resistance between rifampicin and other anti-tubercular drugs. Rifampicin may selectively inhibit the RNA polymerase of the bacterial-dependent DNA and block the synthesis of mRNA, but has no effect on the RNA polymerase of animal molecules.

Isoniazid (H) is also known as rimifon, and the chemical name is 4-pyridylcarbonylhydrazine. Isoniazid is easily soluble in water, slightly soluble in ethanol, and very slightly soluble in ethyl ether. The structure of carbonylhydrazine is not stable, and in acidic or basic condition, it can be hydrolyzed to form isonicotinic acid and hydrazine. The free hydrazine increases the toxicity, and light, heavy metals, temperature, pH, etc can accelerate the hydrolysis thereof.

The molecule structure of isoniazid is as below:

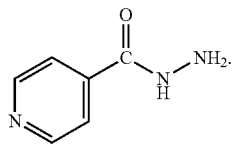

Isoniazid has a good bacterial inhibiting effect on tubercle *bacillus*, and has a good efficacy. The dose of isoniazid is used in a small range, and the toxicity is relatively low, which is easily to be accepted by the patients. The oral absorption rate is 90%, and the serum drug concentration reaches the peak in 1-2 hours after administration. The Vd is 0.61±0.11 L/kg, and the protein binding rate is very low. Isoniazid is mainly used in the progressive stage, dissolving and spreading stage, absorption stage of lung tuberculosis, and also can be used in tubercular meningitis and other extrapulmonary tuberculosis, etc. Isoniazid is usually used in combination with other anti-tubercular drugs in order to enhance the efficacy and overcome the drug-resistant bacteria.

Pyrazinamide (Z) is slightly soluble in water and ethanol, and very slightly soluble in ethyl ether. Pyrazinamide has an effect on accelerating the reaction of rifampicin with isoniazid. The molecule structure of pyrazinamide is as below:

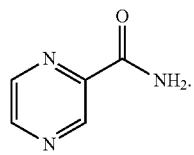

Pyrazinamide has a good bacterial inhibiting effect on human type tubercle *bacillus*, and shows the largest bacterial eliminating effect at pH 5-5.5. In particular, it is the current best bacterial eliminating drug for tubercle *bacillus* slowly growing in phagocyte under acidic condition. The minimum inhibitory concentration of pyrazinamide is 12.5 μg/ml. When it reaches a concentration of 50 μg/ml, pyrazinamide can eliminate tubercle *bacillus*. The intra-cellular concentration of the drug for inhibiting tubercle *bacillus* is 10 folds lower than the extracellular concentration. It almost has no inhibiting effect under neutral and basic conditions. The mechanism may be involved with pyrazinoic acid. When pyrazinamide penetrates into the phagocyte and into the body of tubercle *bacillus*, the amidase in the bacterial body deamidates the amide group of pyrazinamide, converts it to pyrazinoic acid, and exerts the bacterial inhibiting effect. In addition, since pyrazinamide is similar in chemical structure with nicotinamide, pyrazinamide interrupts the dehydrogease by substituting nicotinamide, prevents the dehydrogenation effect, and avoids the utilization of oxygen by tubercle *bacillus*, and thus taking influence on the regular metabolism of the bacteria and causing them to be eliminated.

Ethambutol hydrochloride (E) is easily soluble in water, is easy to absorb moisture, and provides atmosphere for the reaction between rifampicin and isoniazid. The molecule structure of ethambutol hydrochloride is as below:

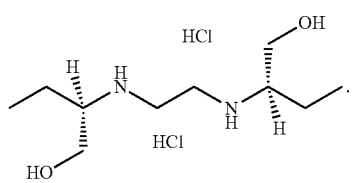

Ethambutol hydrochloride is suitable for treating tuberculosis in combination with other anti-tubercular drugs. The single use of ethambutol hydrochloride tends to generate drug-resistance. Ethambutol hydrochloride has strong activity for the bacteria in the growth and reproduction stage, but has almost no effect on the bacteria in the resting stage.

RHZE combination has a certain importance in clinical practice, but problem also occurs. First, if rifampicin is in direct contacts with isoniazid, they will tend to react with each other, especially in the stomach acidic condition. This makes the bioavailability of rifampicin in a compound drug lower than that of singly used rifampicin, and thus the treatment effect would be compromised or the lower level of rifampicin can generate drug-resistance for patients. It is reported in references (e.g. see Sosa et al, 2005, Ars Pharm, 46:353-364) that under the condition of gastric acid (pH 1-3), the direct contact between rifampicin and isoniazid is easily to react and generate isoniazone. The experiments conducted by Singh et al (see Singh et al, 2000, Pharm. Pharmacol. Commun. 6: 405-410) also demonstrate the fact. It indicates in the research that under the stomach acidic condition, rifampicin decompose to 3-formyl-rifamycin in the absence of isoniazid. In the presence of isoniazid, the generated 3-formyl-rifamycin rapidly reacts with isoniazid, and forms isoniazone via a second order reaction. Since isoniazone is not stable in the acidic condition, it regenerates 3-formyl-rifamycin and isoniazid via a slow first order reaction in a reversible way. In such a complex reaction, rifampicin is further degraded, while isoniazid is recovered. Although isoniazone has some anti-bacterial activity, the anti-bacterial activity is lower than that of rifampicin. Meanwhile, in RHZE combination, pyrazinamide has catalytic effect on the reaction between rifampicin and isoniazid, and ethambutol hydrochloride, which is easy to absorb moisture, provides conditions for the reaction between rifampicin and isoniazid. These are some of the major factors which cause the formulation unstable, and the bioavailability in a compound drug is lower than that in singly used rifampicin. Second, the solubility of rifampicin is also a problem. Rifampicin is a drug having a low solubility, high hyperosmoticity and is easier to dissociate. Its solubility is pH dependent, and shows a large solubility difference in different pH conditions in gastrointestinal tract. Some experiments indicate that at pH 1.4, the solubility reaches about 125 mg/ml, and 80-90% dissolves in 10 minutes. But at pH>3, the solubility is less than 6 mg/ml. If a simple enteric coating method is applied to render rifampicin not to release in stomach, but release in intestinal tract instead, the insolubility of rifampicin in intestinal tract also will directly lead to a decrease of the bioavailability of rifampicin.

Therefore, the problem to be solved by many drug research and development institutions and manufacturers is how to improve the bioavailability of rifampicin in four-ingredient (RHZE) compound formulations. In this regard, some related researches have been reported. For example, WO02/11728 discloses that rifampicin and a pH-dependent carrier are dissolved in media to prepare solid dispersions, so as to increase the solubility of rifampicin. However, the present inventors found in our experiments that since the amount of pH-dependent carrier used is relative low, the large amount release of rifampicin in acidic condition is difficult to control. The patent cannot achieve the same effect of the solid formulation as in the present invention with respect to the bioavailability of rifampicin in RHZE compound drug. The rifampicin solid dispersion in the inventive solid formulation not only increases the solubility and dissolution rate of rifampicin, but also ensures less release or no release of rifampicin in the acidic stomach condition and thus the reduction of the reaction between rifampicin and isoniazid in the body. Meanwhile, the fact that the excipients reduce contact of rifampicin with isoniazid in the formulation ensures the stability of the formulation during storage. The in-vivo and in-vitro stability of rifampicin in the RHZE compound drug facilitates to improve the bioavailability of rifampicin in the compound drug, ensures the therapeutic efficacy and reduces the generation of drug-resistance.

BRIEF SUMMARY OF THE INVENTION

In the first embodiment, the compound oral core-coated solid formulation is in the form of a coated tablet with coated core, comprising rifampicin, isoniazid, pyrazinamide and ethambutol hydrochloride as active ingredients, in which an inner core comprises isoniazid or rifampicin, and is coated with a non-pH dependent water insoluble coating film, and the outer layer of the core-coated solid formulation is coated with a non-pH dependent water soluble coating film which is impermeable barrier to both moisture and light, which, after administration, either rifampicin or isoniazid, or both is less released or not released in the stomach.

In the second embodiment, the compound oral core-coated solid formulation is a three-layer coated tablet, comprising rifampicin, isoniazid, pyrazinamide and ethambutol hydrochloride as active ingredients, in which the top layer and the bottom layer separately and independently comprise one ingredient selected from isoniazid and rifampicin, the central layer comprises at least one of pyrazinamide and ethambutol hydrochloride, and the outside of the threelayer is coated with a non-pH dependent water insoluble coating film, which, after administration, either rifampicin or isoniazid, or both is less released or not released in the stomach.

In the third embodiment, the compound oral core-coated solid formulation is in the form of a coated tablet with coated core, comprising rifampicin, isoniazid, pyrazinamide and ethambutol hydrochloride as active ingredients, in which an inner core comprises isoniazid or rifampicin, and is coated with a non-pH dependent water soluble isolating film, and rifampicin is in the form of rifampicin enteric solid dispersion in which the drug is dispersed in the enteric solid carriers, and the outer layer of the core-coated solid formulation is coated with a non-pH dependent water soluble coating film which is impermeable barrier to both moisture and light.

In the fourth embodiment, the compound oral core-coated solid formulation is in the form of a three-layer coated tablet, comprising rifampicin, isoniazid, pyrazinamide and ethambutol hydrochloride as active ingredients, in which the top layer and the bottom layer independently comprise one ingredient selected from isoniazid and rifampicin, in the layer containing rifampicin, rifampicin is in the form of enteric solid dispersion in which the drug is dispersed in an enteric solid carrier, the central layer comprises at least one of pyrazinamide and ethambutol hydrochloride, the outside of the threelayer is coated with a non-pH dependent water soluble coating film which is impermeable barrier to both moisture and light.

In another embodiment, the non-pH dependent water insoluble coating film in the first and second embodiments comprises a non-pH dependent water insoluble polymeric film-forming material and a plasticizer, optionally, further comprising at least one of a pore-forming agent and an anti-adhesive agent.

In yet another embodiment, the non-pH dependent water insoluble coating film in the second embodiment further comprises an opacifier.

In yet another embodiment, the non-pH dependent water insoluble coating film in the first embodiment further comprises a polymer which disintegrates and expands swiftly when absorbing water, and/or small molecular permeability promoter in the inner core.

In yet another embodiment, the layer containing rifampicin in the second embodiment further comprises a polymer which disintegrates and expands swiftly when absorbing water, the central layer further comprises a retardant.

Not wishing to be bond by any theory, the aim of the compound oral solid formulation design is to render the two active ingredients in the formulation, rifampicin and isoniazid, not to come to contact with each other directly. After administration, at least one of the two active ingredients, rifampicin or isoniazid is controlled so as it would be less released or not released in stomach. The preferred drug releasing amount in the stomach is no more than 15% of the indicated content, more preferably no more than 10%, and further more preferably no more than 5%, so as to improve the chemical stability of the two actives and the bioavailability of the rifampicin in the compound formulation.

In the present invention, the term "a permeability promoter" refers to a substance having a certain osmotic pressure, and thus facilitating the permeation of water and water-soluble molecules. There is no particular limitation on this term in the present invention, provided that the permeability promoter is suitable for using in the pharmaceutical formulation field of the present invention.

In the present invention, the term "a non-pH dependent coating film" refers to a film containing materials whose solubility is non-pH dependent. In the present invention, the term "non-pH dependent substance" means a substance can be dissolved in water and its solubility is not influenced by pH value. There is no particular limitation on this term in the present invention, provided that the non-pH dependent coating film is suitable for using in the pharmaceutical formulation field of the present invention.

In the present invention, the term "an enteric carrier" refers to a substance which is essentially insoluble in the acidic stomach condition, but can be dissolved in the enteric pH condition. There is no particular limitation on this term in the present invention, provided that the enteric carrier is commonly used in the pharmaceutical formulation field of the present invention.

In the present invention, the term "a binder" refers to a tacky substance and it can bind the separate powders together adhesively. There is no particular limitation on this term in the present invention, provided that the binder is commonly used in the pharmaceutical formulation field of the present invention.

In the present invention, the term "a lubricating agent" refers to a substance having an ability to reduce the abrasion and friction caused by contact when placed between two objects which move oppositely. There is no particular limitation on this term in the present invention, provided that the lubricating agent is commonly used in the pharmaceutical formulation field of the present invention.

The present invention relates to a compound oral coating solid formulation, comprising rifampicin, isoniazid, pyrazinamide and ethambutol hydrochloride as active ingredients, in which the active ingredients are composed of a combination of 200 to 300 mg:75 mg to 300 mg:250 to 500 mg:250 to 275 mg, preferably 150 mg:75 mg:400 mg:275 mg.

In one aspect, one technical attribute of the invention is that one or more of the active ingredients in the compound oral coating solid formulation according to the present invention is coated with a non-pH dependent water insoluble coating film. The coating film is water permeable, and is used to control the delayed release of isoniazid or rifampicin, and either rifampicin or isoniazid, together with other active ingredients rapidly release after administration. The design attribute also ensures that rifampicin and isoniazid do not come in direct contact. The compound oral coating solid formulation having the design attribute can be in the form of a coated tablet with coated core or a three-layer coated tablet.

In one preferred embodiment of the present invention, the compound oral solid formulation according to the present invention is in the form of a coated tablet with coated core, in which the inner layer is a isoniazid layer which may be in the form of one or more independent granules, pellets and flakes coated with a non-pH dependent water insoluble coating film. The coated inner core is coated with the outer layer containing rifampicin, pyrazinamide and ethambutol hydrochloride, and thus forms the coated tablet with coated core. The coated tablet with coated core is coated with a non-pH dependent water soluble coating film which is impermeable barrier to both moisture and light.

In the coated tablet with coated core, in addition to the active ingredients, the inner core of the non-pH dependent water insoluble coating film may also contains a polymer which disintegrates and expands swiftly when absorbing water, and optionally contains one or more carriers selected from permeability promoter having a small molecule weight, a binder and a lubricating agent. The polymer which disintegrates and expands swiftly when absorbing water is one or more selected from the group consisting of cross-linked sodium carboxymethyl cellulose (CCMC-Na), low-substituted hydroxypropyl cellulose (L-HPC), sodium carboxymethyl cellulose (CMC-Na), sodium carboxymethyl starch (CMS-Na), polyvinylpolypyrrolidone (PVPP) and microcrystalline cellulose (MCC). The permeability promoter having a small molecule weight is a substance selected from the group consisting of sodium chloride and potassium chloride.

In the coated tablet with coated core, the non-pH dependent water insoluble coating film over-coating the inner isoniazid core layer constitutes 6 to 30% by weight of the inner isoniazid core layer. The film has water permeability, and contains a non-pH dependent water insoluble polymeric film-forming material, plasticizer, and optionally contains pore-forming agent and/or anti-adhesive agent. The film-forming material in the non-pH dependent water insoluble coating film constitutes 70 to 90%, preferably 70 to 80% by weight of the total weight of the coating film. The film-forming material is a substance preferably selected from the group consisting of Aquacoat ECD, ethyl cellulose (EC), cellulose acetate (CA), polyvinyl chloride, polycarbonate, vinyl alcohol-vinyl acetate, and a combination thereof. The plasticizer constitutes 10 to 30%, preferably 13 to 25% by weight of the total weight of the coating film. The plasticizer is a substance preferably selected from the group consisting of triethyl citrate (TEC), tributyl citrate (TBC), acetyl triethyl citrate (ATEC), dimethyl sebacate (DMS), dibutyl sebacate (DBS), dibutyl phthalate (DBP), and a combination thereof. The pore-forming agent constitutes 0 to 15%, preferably 4 to 13% by weight of the total weight of the coating film. The pore-forming agent is a substance preferably selected from the group consisting of polyethylene glycols, hydroxypropyl methylcellulose, Kollicoat® IR, polyvinyl alcohol, urea, and a combination thereof. The anti-adhesive agent constitutes 0 to 25%, preferably 0 to 15% by weight of the total weight of the coating film. The anti-adhesive agent is a substance preferably selected from the group consisting of talc powder, light finely-divided silica gel, and a combination thereof.

The preparation method of the coated tablet with coated core is as below:

1) The Preparation of the Inner Core:

Isoniazid and a polymer which disintegrates and expands swiftly when absorbing water and/or permeability promoter having a small molecule weight are mixed, grinded, granulated or pelleted, and then dried and coated with a non-pH dependent water insoluble coating film. If it is required to be prepared as the inner core of a coated tablet, glidant or lubricating agent are necessary to be added to the prepared granules, homogenized, sieved, and then compressed to form a tablet, which is subsequently coated with a non-pH dependent water insoluble coating film.

2) The Preparation of the Outer Layer Granules:

Rifampicin, pyrazinamide and ethambutol hydrochloride are subjected to mixing with filler and disintegration, and then granulated with a binder, dried, added glidant or lubricating agent therein, homogenized, sieved and then ready to use.

3) The Compression of the Coated Tablet with Coated Core:

The core of the coated tablet with coated core in step 1) is used as the inner core, and the granules in step 2) are used as the outer layer. The coated tablet with coated core is formed by compression, or the coated granules or coated pellets in step 1) are mixed with the granules in step 2) and then compressed to form a tablet.

4) Coating:

The coated tablet with coated core in step 3) is subjected to coating with a non-pH dependent water soluble coating film which is impermeable barrier to both moisture and light.

In another preferred embodiment, the compound oral solid formulation according to the present invention is in the form of a three-layer coated tablet, consisting of a top layer, central layer and bottom layer, in which the top layer and the bottom layer is respectively the rifampicin layer and the isoniazid/pyrazinamide layer, and the central layer is the ethambutol hydrochloride layer. The rifampicin layer comprises a polymer which disintegrates and expands swiftly when absorbing water. The ethambutol hydrochloride layer contains a retardant which delays the quick disintegration or release of ethambutol hydrochloride and other pharmaceutical carriers. The isoniazid/pyrazinamide layer comprises other pharmaceutical carriers. The three-layer tablet is coated with a non-pH dependent water insoluble coating film.

The non-pH dependent water insoluble coating film over-coating the three-layer tablet has water permeatability, and it constitutes 5 to 12% by weight of the uncoated three-layer tablet core. The film comprises a non-pH dependent water insoluble polymeric film-forming material, a plasticizer, optionally further comprising at least one of pore-forming agent, opacifier, anti-adhesive agent. The non-pH dependent water insoluble polymeric film-forming material is a substance selected from the group consisting of Aquacoat ECD, ethyl cellulose (EC), cellulose acetate (CA), polyvinyl chloride, polycarbonate, vinyl alcohol-vinyl acetate, and a combination thereof. The non-pH dependent water insoluble polymeric film-forming material constitutes 50 to 80% by weight of the total weight of the coating film. The plasticizer is a substance selected from the group consisting of triethyl citrate (TEC), tributyl citrate (TBC), acetyl triethyl citrate (ATEC), dimethyl sebacate (DMS), dibutyl sebacate (DBS), dibutyl phthalate (DBP), and a combination thereof. The plasticizer constitutes 20 to 45% by weight of the total weight of the coating film. The pore-forming agent is a substance selected from the group consisting of polyethylene glycols, hydroxypropyl methylcellulose, Kollicoat® IR, polyvinyl alcohol, urea, and a combination thereof. The pore-forming agent constitutes 0 to 15% by weight of the total weight of the coating film. The anti-adhesive agents a substance preferably selected from the group consisting of talc powder, light finely-divided silica gel, and a combination thereof. The anti-adhesive agent constitutes 0 to 20% by weight of the total weight of the coating film. The opacifier is titanium dioxide. The opacifier constitutes 0 to 20% by weight of the total weight of the coating film.

The rifampicin layer of the three-layer coated tablet comprises the polymer which disintegrates and expands swiftly when absorbing water, and the polymer is one or more selected from the group consisting of crosslinked sodium carboxymethyl cellulose (CCMC-Na), low-substituted hydroxypropyl cellulose (L-HPC), sodium carboxymethyl cellulose (CMC-Na), sodium carboxymethyl starch (CMS-Na), polyvinylpolypyrrolidone (PVPP) and microcrystalline cellulose (MCC).

The ethambutol hydrochloride layer of the three-layer coated tablet comprises a retardant, which is one or more selected from the group consisting of water insoluble skeleton material, such as ethyl cellulose, polyethylenes, acrylic resins; erosive skeleton material, such as beeswax, hydrogenated vegetable oil, stearic acid, polyethylene glyol, carnauba wax, glycerol stearate, propylene glycol stearate, and stearyl alcohol; and water soluble skeleton material, such as hydroxypropyl methylcellulose, polyethylene oxide (PEO).

The preparation method of the three-layer coated tablet is as below:

1) The Preparation of the Rifampicin Layer:

Rifampicin and a polymer which disintegrates and expands swiftly when absorbing water are mixed, grinded, sieved, granulated with a binder, and then dried. Glidant or lubricating agent are added, homogenized, sieved, and then ready for compression into tablet.

2) The Preparation of the Ethambutol Hydrochloride Layer:

Ethambutol hydrochloride, a retardant and a filler are mixed, grinded, sieved, granulated with a binder, and then dried. Glidant or lubricating agent are added, homogenized, sieved, and then ready for compression into tablet.

3) The Preparation of the Isoniazid/Pyrazinamide Layer:

Isoniazid, pyrazinamide and a filler are mixed, grinded, sieved, granulated with a binder, and then dried. Glidant or lubricating agent are added, homogenized, sieved, and then ready for compression into tablet.

4) The Compression the Three-Layer Tablet:

The granules in step 1), 2), and 3) are compressed respectively as the top, central and bottom layers.

5) Coating:

The three-layer tablet in step 4) is subjected to coating with a non-pH dependent water insoluble coating film.

On the other aspect, another design attribute of the present invention lies in that since rifampicin is a less soluble drug, enteric solid dispersion technology is used to increase the solubility and dissolution rate of rifampicin, thus the bioavailability of rifampicin in the formulation is improved. At the same time, it also improves the stability of the drug in the compound formulation according to the present invention. The design attribute lies in that the compound oral solid formulation is a coated tablet with coated core or a three-layer coated tablet.

In one preferred embodiment of the present invention, the compound oral core-coated solid formulation is in the form of a coated tablet with coated core, in which the inner core comprises isoniazid or rifampicin, and is coated with a non-pH dependent water soluble isolating film. And, rifampicin is in the form of rifampicin enteric solid dispersion, in which the drug is dispersed as solid solution in the enteric solid carriers. The outer layer of the core-coated solid formulation is coated with a non-pH dependent water soluble coating film which is impermeable barrier to both moisture and light.

The weight ratio of rifampicin in the rifampicin solid dispersions according to the present invention and the enteric carrier ranges in 2:1 to 1:3, in which the enteric solid dispersions carrier is one or more selected from the group consisting of: polyvinyl acetate phthalate (PVAP), methacrylic acid/methyl methacrylate copolymer, such as Eudragit L30D-55, Eudragit L100, Eudragit S100; cellulose and its derivatives, such as cellulose acetate phthalate (CAP), cellulose acetate trimellitate (CAT), hydroxypropyl methyl cellulose phthalate (HPMCP), hydroxypropyl methyl cellulose trimellitate (HPMCT); cellulose acetate succinate (CAS) and hydroxypropyl methyl cellulose acetate succinate (HPMCAS), hydroxypropyl methyl cellulose acetate phthalate (HPMCAP), and hydroxypropyl methyl cellulose acetate succinate (HPMCAS) is preferred.

The non-pH dependent water soluble polymeric film-forming material is a substance selected from the group consisting of hydroxypropyl methylcellulose (HPMC), Kollicoat® IR, Opadry II, and a combination thereof.

The preparation method for the rifampicin solid dispersion in the present invention can be the conventional methods for the preparation of solid dispersions, such as hot melting method, spray drying method, one-step fluidized bed method or solvent evaporation method.

The preparation method of the coated tablet with coated core is as below:

1) The Preparation of the Inner Core:

Isoniazid and a filler are mixed, grinded, granulated or pelleted with a binder, and then dried and coated with non-pH dependent water soluble separating coating film; If it is required to be prepared as the inner core of a coated tablet, glidant or lubricating agent are necessary to be added to the prepared granules, homogenized, sieved, and then compressed to form a tablet, which is subsequently coated with a non-pH dependent water soluble coating film as the separating coating film.

2) The Preparation of the Outer Layer Granules:

First, rifampicin is formed into an enteric solid dispersion, and then the produced rifampicin solid dispersion, pyrazinamide and ethambutol hydrochloride are subjected to mixing with a filler, a disintegrant and granules made by a binder, added glidant or lubricating agent therein, homogenized, sieved and then ready to use.

3) The Compression of the Coated Tablet with Coated Core:

The core of the coated tablet with coated core in step 1) is used as the inner core, and the granules in step 2) are used as the outer layer. The coated tablet with coated core is formed by compression, or the coated granules or coated pellets in step 1) are mixed with the granules in step 2) and then compressed to form a tablet.

4) Coating:

The coated tablet with coated core in step 3) is subjected to coating with a non-pH dependent water soluble coating film which is impermeable barrier to both moisture and light.

In another preferred embodiment, the compound oral solid formulation is a three-layer coated tablet, the top layer and bottom layer of which each independently comprise any of isoniazid and rifampicin. In the rifampicin containing layer, rifampicin is in the form of rifampicin enteric solid dispersion which disperses in the enteric solid carriers. The central layer comprises at least one of pyrazinamide and ethambutol hydrochloride. The outside of the threelayer is coated with a non-pH dependent water soluble coating film which is impermeable barrier to both moisture and light. The weight ratio range of rifampicin and the enteric carrier, the preparation methods of the enteric solid carrier and rifampicin solid dispersion are described above.

The preparation method of a three-layer coated tablet is as below:

1) The Preparation of the Rifampicin Layer:

First, rifampicin is formed into an enteric solid dispersion, and then the produced rifampicin solid dispersion and other pharmaceutical carriers are mixed, granulated or directly used for compression as a tablet;

2) The Preparation of the Ethambutol Hydrochloride Layer:

Ethambutol hydrochloride and other pharmaceutical carriers are mixed, grinded, sieved, and then granulated with binder, dried, added glidant or lubricating agent therein, homogenized, sieved and then ready to use;

3) The Preparation of the Isoniazid/Pyrazinamide Layer:

Isoniazid, pyrazinamide and other pharmaceutical carriers are mixed, grinded, sieved, and then granulated with binder, dried, added glidant or lubricating agent therein, homogenized, sieved and then ready to use;

4) The Compression of the Three-Layer Tablet:

The granules in step 1), 2), and 3) are compressed respectively as the top, central and bottom layers.

5) Coating:

The three-layer tablet in step 4) is subjected to coating with a non-pH dependent water insoluble coating film.

The non-pH dependent water soluble coating film which is impermeable barrier to both moisture and light in the above embodiments comprises a substance selected from the group consisting of Kollicoat® IR, hydroxypropyl methylcellulose (HPMC), a combination of titanium dioxide and talc powder, and Opadry II containing the combination of hydroxypropyl methylcellulose (HPMC), titanium dioxide and talc powder.

The compound oral core-coated solid formulation according to the present invention may also comprises other pharmaceutical carriers selected from the group consisting of a filler, a binder, a lubricating agent or a glidant and/or a disintegrant.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 schematically shows a coated tablet with coated core, A: inner core; B: inner core coating film; C: outer layer; D: coating film;

FIG. 2 schematically shows a three-layer coated tablet; A: top layer; B: central layer; C: bottom layer; D: coating film;

FIG. 3 shows the HPLC chromatogram measuring the related substances of the rifampicin bulk drug of batch No. 0811011 on day 0;

FIG. 4 shows the HPLC chromatogram measuring the related substances of the rifampicin solid dispersion (sample according to Example 8) prepared by spray drying method on day 0;

FIG. 5 shows the HPLC chromatogram measuring the related substances of the rifampicin solid dispersion (sample according to Example 11) prepared by solvent spontaneous evaporation method on day 0;

FIG. 6 shows the HPLC chromatogram measuring the related substances of the rifampicin solid dispersion (sample according to Example 7) prepared by hot melting method on day 0;

FIG. 7 shows the HPLC chromatogram measuring the related substances of an imported product after accelerated experiment (40° C., 75% RH) for 6 months;

FIG. 8 shows the HPLC chromatogram measuring the related substances of the inventive coated tablet with coated core after accelerated experiment (40° C., 75% RH) for 6 months;

FIG. 9 shows the HPLC chromatogram measuring the related substances of the inventive coated tablet with coated core after accelerated experiment (25° C., 60% RH) for 12 months;

FIG. 10 shows the profiles of time vs. drug blood level after singly administrating beagles with the inventive rifampicin (sample according to Example 11) and commercially available rifampicins;

FIG. 11 shows the profiles of time vs. drug blood level after administrating beagle with the inventive rifampicin+ commercially available isoniazid and commercially available rifampicin+commercially available isoniazid.

DETAILED DESCRIPTION OF THE INVENTION

Examples

The present invention will be further illustrated by way of example, and is not intended to limit the present invention thereto.

Example 1

The Preparation of a Coated Tablet with Coated Core

1) The Preparation of the Uncoated Core of the Tablet 75.00 g of isoniazid, 2.00 g of sodium chloride, 18.70 g of microcrystalline cellulose, and 10.30 g of crosslinked sodium carboxymethyl cellulose were mixed homogenously, and then were grinded to pass through a sieve with a pore size of 0.250 mm. A flexible material was made by the use of 2% hydroxypropyl methyl cellulose, and then was passed through a sieve with a pore size of 0.710 mm and granulated. The mixture was dried at 50° C. until the water content of the granules was less than 3.0%. 1% by weight of magnesium stearate on the dry granule basis was added. The mixture was further mixed and passed through a sieve with a pore size of 0.85 mm, and then was mixed homogenously and compressed to form a tablet by a 4*9 mm stamping die with specific shape. The pressure was controlled at 50 to 65 N. The disintegration time of the tablet core before coating is most preferably controlled within 1 minute.

2) The Coating of the Inner Core of the Tablet

A coating solution in a solid content of 15% was prepared according to the solid content weight ratio of Aquacoat ECD:triethyl citrate (TEC):Kollicoat® IR=8.05:2.01:0.50. The temperature of the coating bed was controlled in the range of 39° C. to 42° C. The weight gain was 8 to 10%. The mixture is cured at 60° C. for 2 hours after coating, and was ready to use as the inner core of the coated tablet with coated core. The releasing profile of isoniazid in the inner core of the coated tablet with coated core is shown in Table 1.

3) The Preparation of the Compression of the Outer Layer Granules 150.00 g of rifampicin, 400.00 g of pyrazinamide, 275.00 g of ethambutol hydrochloride, 160.00 g of microcrystalline cellulose and 54.00 g of low-substituted hydroxypropyl cellulose were mixed homogenously, and then formed into powder. The mixture was passed through a sieve with a pore size of 0.250 mm, and granulated by the use of 5% hydroxylpropyl methyl cellulose. The mixture was dried at 50° C., and the moisture of the granules was controlled less than 3%. 0.5% of finely-divided silica gel on the dry granule basis was added, and the mixture was passed through a sieve with a pore size of 0.600 mm. The resulting product was compressed to the coated tablet with coated cores.

4) The Preparation of the Outer Layer

A 20% concentration of Opadry II coating solution was prepared. The temperature of the coating materials was controlled at 40 to 45° C. The weight gain was about 3%.

Example 2

The Preparation of Coated Tablet with Coated Core

1) The Preparation of the Uncoated Core of the Tablet 75.00 g of isoniazid, 18.70 g of microcrystalline cellulose, 8.20 g of crosslinked sodium carboxymethyl cellulose were mixed homogenously, and then were grinded to pass through a sieve with a pore size of 0.250 mm. A flexible material was made by the use of 2% hydroxypropyl methyl cellulose, and then passed through a sieve with a pore size of 0.710 mm and granulated. The mixture was dried at 50° C. until the water content of granules was less than 3.0%. 1% of magnesium stearate on the dry granule basis were added. The mixture was mixed and passed through a sieve with a pore size of 0.85 mm, and then was mixed homogenously and compressed to form a tablet by a round stamping die with a 6.5 dimple. The pressure was controlled at 50 to 65 N. The disintegration time of the tablet core before coating is optimum within 1 minute.

2) The Coating of the Inner Core of the Tablet

A coating solution in a solids content of 15% was prepared according to the solid content weight ratio of Aquacoat ECD:triethyl citrate (TEC):Kollicoat® IR=8.05:2.01:0.50. The temperature of the coating bed was controlled in the range of 39° C. to 42° C. The weight gain was 8 to 10%. The mixture is cured at 60° C. for 2 hours after coating, and was ready to use as the inner core of the coated tablet with coated core. The releasing profile of isoniazid in the inner core of the coated tablet with coated core is shown in Table 2.

3) The Compression and Coating of the Coated Tablet with Coated Core

The outer layer granules in Example 1 were used to compress the coated tablet with coated core, the resulting tablet was coated with 20% concentration of Opadry II coating solution. The temperature of the coating materials was controlled in the range of 40 to 45° C. The weight gain was about 3%.

Example 3

The Preparation of Coated Tablet with Coated Core

1) The Preparation of the Uncoated Core of the Tablet 75.00 g of isoniazid, 18.70 g of microcrystalline cellulose, 8.20 g of crosslinked sodium carboxymethyl cellulose were mixed homogenously, and then were grinded to pass through a sieve with a pore size of 0.250 mm. A flexible material was made by the use of 2% hydroxypropyl methyl cellulose. First, isoniazid was grinded and passed through a sieve with a pore size of 0.250 mm. The mixture was extruded with a sieve with a pore size of 600 μm. The mixture was rounded at 700 rpm, and then produced as pellets. The pellets were dried at 50° C.

2) The Coating of the Pellet Core

A coating solution in a solid content of 15% was prepared according to the solid content weight ratio of Aquacoat ECD:triethyl citrate (TEC):Kollicoat® IR=8.05:2.01:0.50. The temperature of the coating bed was controlled in the range of 39° C. to 42° C. The weight gain of the coating of pellets was 22 to 25%. The mixture is cured at 60° C. for 2 hours after coating, and was ready to use as the inner core of the coated tablet with coated core.

3) The Compression and Coating of the Coated Tablet with Coated Core

The outer layer granules in Example 1 were used to compress to form a tablet according to the ratio of isoniazid:rifampicin:pyrazinamide:ethambutol hydrochloride in 75 mg:150 mg:400 mg:275 mg, the resulting tablet was coated with 20% concentration of Opadry II coating solution. The temperature of the coating materials was controlled at 40 to 45° C. The weight gain was about 3%.

Example 4

The Preparation of a Three-Layer Coated Tablet

1) The Preparation of Granules of Rifampicin Layer 30.03 g of isoniazid, 5.60 g of microcrystalline cellulose, 7.40 g of crosslinked sodium carboxymethyl cellulose were mixed homogenously, and then were grinded to pass through a sieve with a pore size of 0.250 mm. The mixture was passed through a sieve with a pore size of 0.710 mm with a 2% hydroxypropyl methyl cellulose solution. The mixture was dried at 50° C. until the water content of granules was less than 3.0%. 0.5% of finely-divided silica gel was added on the dry granule basis, and the mixture was passed through a sieve with a pore size of 0.850 mm. The resulting product was mixed homogenously and ready for compression into tablet.

2) The Preparation of Granules of Ethambutol Hydrochloride Layer 55.02 g of ethambutol hydrochloride and 5.02 g microcrystalline cellulose were mixed, grinded, and passed through a sieve with a pore size of 0.250 mm. The mixture was passed through a sieve with a pore size of 0.710 mm with an ethanol/water solution of 5% ethyl cellulose (ethanol:distilled water=90:10, v/v) and was granulated. The mixture was dried at 80° C. until the water content of granules was less than 2.0%. 0.5% of stearic acid was added on the dry granule basis, and the mixture was passed through a sieve with a pore size of 0.850 mm. The resulting product was mixed homogenously and ready for compression into tablet.

3) The Preparation of the Granules of Isoniazid/Pyrazinamide Layer 15.00 g of ethambutol hydrochloride, 80.00 g of pyrazinamide and 8.02 g microcrystalline cellulose were mixed, grinded, and passed through a sieve with a pore size of 0.250 mm. The mixture was passed through a sieve with a pore size of 0.710 mm with an aqueous solution of 2% hydroxypropyl methyl cellulose, and granulated. The mixture was dried at 80° C. until the water content of granules was less than 3.0%. 0.5% of stearic acid was added on the dry granule basis, and the mixture was passed through a sieve with a pore size of 0.850 mm. The resulting product was mixed homogenously and ready for compression into tablet.

4) Compression for Tablet

Rifampicin layer, ethambutol hydrochloride layer, and isoniazid/pyrazinamide layer were compressed to a three-layer tablet according to ratio of rifampicin:ethambutol hydrochloride:isoniazid:pyrazinamide=150 mg:275 mg:75 mg:400 mg.

5) Coating

A 15% coating solution was prepared according to the solid weight content of Aquacoat ECD:DBS:TEC:titanium dioxide=60:20:10:10. The weight gain of the coating was about 8%. It was cured at 60° C. for 2 h.

Example 5

The Preparation of a Three-Layer Coated Tablet

1) The Preparation of Rifampicin Layer Granules 30.13 g of isoniazid, 5.66 g of microcrystalline cellulose, 7.50 g of crosslinked sodium carboxymethyl cellulose were mixed homogenously, and then were grinded to pass through a sieve with a pore size of 0.250 mm. The mixture was passed through a sieve with a pore size of 0.710 mm with a 2% hydroxypropyl methyl cellulose solution. The mixture was dried at 50° C. until the water content of granules was less than 3.0%. 0.5% of finely-divided silica gel was added on the dry granule basis, and the mixture was passed through a sieve with a pore size of 0.850 mm. The resulting product was mixed homogenously and ready for compression into tablet.

2) The Preparation of Granules of Ethambutol Hydrochloride Layer 55.22 g of ethambutol hydrochloride, 5.99 g microcrystalline cellulose and 3.01 g of hydroxylpropyl cellulose K100M were mixed, grinded, and passed through a sieve with a pore size of 0.250 mm. A flexible material made by the use of 70% ethanol/water solution (v/v) was passed through a sieve with a pore size of 0.710 mm and granulated. The mixture was dried at 80° C. until the water content of granules was less than 2.0%. 0.5% of stearic acid was added on the dry granule basis, and the mixture was passed through a sieve with a pore size of 0.850 mm. The resulting product was mixed homogenously and ready for compression into tablet.

3) The Preparation of Granules of Isoniazid/Pyrazinamide Layer 15.08 g of isoniazid, 80.10 g of pyrazinamide, and 8.10 g of microcrystalline cellulose were mixed and grinded to pass through a sieve with a pore size of 0.250 mm. The mixture was passed through a sieve with a pore size of 0.710 mm with a 2% hydroxypropyl methyl cellulose solution. The mixture was dried at 80° C. until the water content of granules was less than 3.0%. 0.5% of stearic acid was added on the dry granule basis, and the mixture was passed through a sieve with a pore size of 0.850 mm. The resulting product was mixed homogenously and ready for compression into tablet.

4) Compression for Tablet

Rifampicin layer, ethambutol hydrochloride layer, and isoniazid/pyrazinamide layer were compressed to a three-layer tablet according to ratio of rifampicin:ethambutol hydrochloride:isoniazid:pyrazinamide=150 mg:275 mg:75 mg:400 mg.

5) Coating

A 15% coating solution was prepared according to the solid weight content of Aquacoat ECD:DBS:TEC:titanium dioxide=60:20:10:10. The weight gain of the coating was about 8%. It was cured at 60° C. for 2 h.

Example 6

A 15% coating solution was prepared according to the solid weight content of Aquacoat ECD:TEC:HPMC:titanium dioxide=70.8:12.5:8.3:8.3. The weight gain of the coating was about 8%. It was cured under 60° C. for 2 h.

Example 7

The Preparation of the Coated Tablet with Coated Core

1) The Preparation of the Uncoated Core of the Tablet 15.02 g of isoniazid and 2.80 g of microcrystalline cellulose were mixed homogenously, and then were grinded to pass through a sieve with a pore size of 0.250 mm. A flexible material was made by the use of 2% hydroxypropyl methyl cellulose, and then passed through a sieve with a pore size of 0.710 mm and granulated. The mixture was dried at 50° C. until the water content of granules was less than 3.0%. 1% of magnesium stearate on the dry granule basis were added. The mixture was mixed and passed through a sieve with a pore size of 0.85 mm, and then was mixed homogenously and compressed to form a tablet by a 4*9 mm stamping die with specific shape. The pressure was controlled at 50 to 65 N.

2) The Coating of the Inner Core of the Tablet with Separating Coating Film

A 10% HPMC solution was used to coat. The temperature of the coating bed was controlled in the range of 28° C. to 32° C. The weight gain was about 5%.

3) The Preparation of Rifampicin Solid Dispersion in Outer Layer 15.05 g of rifampicin and 15.10 g of hydroxypropyl methyl cellulose acetate succinate were mixed homogenously. The rifampicin solid dispersion was prepared by hot melting method, and then grinded and passed through a sieve with a pore size of 0.250 mm.

4) The Preparation of the Granules of Pyrazinamide/ Ethambutol Outer Layer 400.70 g of rifampicin, 275.05 g of ethambutol hydrochloride, 161.04 g of microcrystalline cellulose and 54.50 g of low-substituted hydroxypropyl cellulose were mixed homogenously, and then formed into powder. The mixture was passed through a sieve with a pore size of 0.250 mm, and granulated with 5% hydroxylpropyl methyl cellulose. The mixture was dried, and the moisture of the granules was controlled less than 3%.

5) The Mixing of Outer Layer Granules

The rifampicin solid dispersion powders were mixed with dried pyrazinamide/ethambutol hydrochloride granules in step 4) according to the ratio of rifampicin:ethambutol hydrochloride:pyrazinamide=150 mg:275 mg:400 mg. A 0.5% of finely-divided silica gel was added based on mixed granules, and passed through a sieve with a pore size of 0.600 mm. The resulting product was ready for compression into tablet.

6) The Compression of the Coated Tablet with Coated Core

The coated tablet in step 2) was used as the tablet core, and the granules produced in step 5) were used as the outer layer and compressed to the coated tablet with coated core.

7) The Coating of the Outer Layer

A 20% concentration of Opadry II coating solution was prepared. The temperature of the coating materials was controlled at 40 to 45° C. The weight gain was about 3%.

Example 8

The Preparation of Coated Tablet with Coated Core

1) The Preparation of Rifampicin Solid Dispersion in Outer Layer 150.00 g of rifampicin and 150.00 g of hydroxypropyl methyl cellulose acetate succinate were mixed homogeneously, then dissolved in 1500.0 g of dichloromethane and 1500.0 g acetone respectively, the resulting solutions were mixed homogeneously, and then the rifampicin solid dispersion was prepared by spray drying method. The air blowing temperature was controlled at 50 to 55° C.

2) The Mixing of Outer Layer Granules

The rifampicin solid dispersion powders prepared by spray drying method were mixed with dried pyrazinamide/ ethambutol hydrochloride granules in step 4) of Example 7 according to the ratio of rifampicin:ethambutol hydrochloride:pyrazinamide=150 mg:275 mg:400 mg. A 0.5% of finely-divided silica gel was added on the mixed granule basis, and passed through a sieve with a pore size of 0.600 mm. The resulting product was ready for compression into tablet.

3) The Compression of the Coated Tablet with Coated Core

The coated tablet in step 2) of Example 7 was used as the tablet core, and the granules produced in step 2) of Example 8 were used as the outer layer and compressed to the coated tablet with coated core.

4) The Coating of the Outer Layer

A 20% concentration of Opadry II coating solution was prepared. The temperature of the coating materials was controlled at 40 to 45° C. The weight gain was about 3%.

Example 9

The Preparation of Coated Tablet with Coated Core

1) The Preparation of the Rifampicin Solution 150.00 g of rifampicin and 150.00 g of hydroxypropyl methyl cellulose acetate succinate were mixed homogeneously, then dissolved in 1500.0 g of dichloromethane and 1500.0 g acetone respectively, the resulting solutions were mixed homogeneously for subsequent use.

2) The Preparation of the Outer Layer Granules 400.00 g of pyrazinamide, 275.00 g of ethambutol hydrochloride, 160.00 g of microcrystalline cellulose and 54.00 g of low-substituted hydroxypropyl cellulose were mixed homogenously, and grinded. The mixture was passed through a sieve with a pore size of 0.250 mm, and then poured into a fluidized bed. The rifampicin solution in step 1) was used in one-step granulation method. The temperature of the materials was controlled at 35 to 40° C., and the water content of the granules was controlled less than 3%. A prescription amount of finely-divided silica gel was added, and passed through a sieve with a pore size of 0.600 mm. The resulting product was ready for use.

3) The Compression of the Coated Tablet with Coated Core

The coated tablet in step 2) of Example 7 was used as the tablet core, and the granules produced in step 2) of Example 9 were used as the outer layer and compressed to the coated tablet with coated core.

4) The Coating of the Outer Layer

A 20% concentration of Opadry II coating solution was prepared. The temperature of the coating materials was controlled at 40 to 45° C. The weight gain was about 3%.

Example 10

The Preparation of a Three-Layer Coated Tablet

1) The Preparation of the Rifampicin Layer Granules 60.30 g of rifampicin solid dispersion in Example 8, 5.60 g of microcrystalline cellulose, 7.32 g of crosslinked sodium carboxymethyl cellulose were mixed homogenously, and then were grinded to pass through a sieve with a pore size of 0.250 mm. The mixture was passed through a sieve with a pore size of 0.710 mm with a 2% hydroxypropyl methyl cellulose solution. The mixture was dried at 50° C. until the water content of granules was less than 3.0%. 0.5% of stearic acid was added on the dry granule basis, and the mixture was passed through a sieve with a pore size of 0.850 mm. The resulting product was mixed homogenously and ready for compression into tablet.

2) The Preparation of Granules of Ethambutol Hydrochloride Layer 55.22 g of ethambutol hydrochloride and 6.03 g microcrystalline cellulose were mixed, grinded, and passed through a sieve with a pore size of 0.250 mm. The mixture was passed through a sieve with a pore size of 0.710 mm with an aqueous solution of 5% hydroxypropyl methyl cellulose and granulated. The mixture was dried at 80° C. until the water content of granules was less than 2.0%. 0.5% of stearic acid was added on the dry granule basis, and the mixture was passed through a sieve with a pore size of 0.850 mm. The resulting product was mixed homogenously and ready for compression into tablet.

3) Compression for Tablet

1) Rifampicin layer, 2) ethambutol hydrochloride layer, and 3) isoniazid/pyrazinamide layer in Example 5 were compressed to a three-layer tablet according to the ratio of rifampicin:ethambutol hydrochloride:isoniazid:pyrazinamide=150 mg:275 mg:75 mg:400 mg.

4) Coating

A 20% concentration of Opadry II coating solution was prepared. The temperature of the coating materials was controlled at 40 to 45° C. The weight gain was about 3%.

Example 11

148.84 g of rifampicin solid dispersion in Example 8, 20.75 g of microcrystalline cellulose, 8.94 g carbonoxymethyl cellulose sodium and 0.90 g of finely-divided silicone gel were mixed homogenously and compressed to form a tablet by a round stamping die with a 12 dimple. The pressure was controlled at 50 to 90 N. The resulting tablet was coated with a 20% concentration of Opadry II coating solution. The temperature of the coating materials was controlled at 40 to 45° C. The weight gain was about 3%. The in vivo experimental data of the formulation in the Example are shown in Tables 10 to 11.

Example 12

Rifampicin solid dispersions with different ratios are prepared by means of solvent spontaneous evaporation method. 9.0, 6.0, 3.0, 1.5 and 1.0 g of HPMCAS were each dissolved in 30.0 g of dichloromethane to prepare a solution. And then, the rifampicin solutions were each poured into the HPMCAS solution. After mixed homogeneously for 1 h, the mixtures were each poured into watch glasses, and placed in the hood for evaporating to dry. The rifampicin solid dispersions were obtained, and then grinded for use. The measurement results of the release degree of rifampicin in the formulation of the Example were shown in Table 5.

Materials

Rifampicin (Shenyang Antibiotics Factory); isoniazid (Zhejiang Xinsai Pharmaceuticals Co. Ltd.); pyrazinamide (Jiangsu Sihuan Biotec Co. Ltd.); ethambutol hydrochloride (Shanghai Wuzhou Pharmaceuticals Co. Ltd.); The imported TB4 coated tablet with coated core (Panacea Biotec Ltd); rifampicin capsules made in China (Shenyang Hongqi pharmaceuticals Co. Ltd.); isoniazid tablet made in China (Shenyang Hongqi pharmaceuticals Co. Ltd.); microcrystalline cellulose (Asahi Kasei Chemicals Corporation); low-substituted hydroxypropyl cellulose (Shin-Etsu); hydroxypropyl methylcellulose E5 and K100M (Colorcon); stearic acid (Hunan Huari Pharmaceuticals Co. Ltd.); finely-divided silicone gel (Evonik); hydroxypropyl methyl cellulose acetate succinate (Shin-Etsu); crosslinked sodium carboxymethyl cellulose (Nichirin Chemical Industries Ltd.); Aquacoat ECD (FMC Biopolymer); triethyl citrate (Shanghai Shenbao Flavours and Perfumes Co. Ltd.); Kollicoat® IR (BASF); magnesium stearate (Anhui Shanhe Pharmaceutic Adjuvant Co. Ltd.); Vitamin C (Hebei Welcome Pharmaceutical Co., Ltd); lauryl sodium sulfate (Anhui Shanhe Pharmaceutic Adjuvant Co. Ltd.); PEG6000 (Chemical Reagents Co. Ltd., Sinopharm Group); Opadry II (Colorcon); dichloromethane (Chemical Reagents Co. Ltd., Sinopharm Group); acetone (Chemical Reagents Co. Ltd., Sinopharm Group); sodium chloride (Shanghai Qingxi Chemical Technology Co. Ltd.); acetonitrile (chromatographically pure, MERCK Co. Ltd., US); anhydrous disodium hydrogen phosphate (analytically pure, Shanghai Lingfeng Chemical Reagent Co. Ltd.); phosphoric acid (analytically pure, Chemical Reagents Co. Ltd., Sinopharm Group); sodium hydroxide (analytically pure, Shanghai Lingfeng Chemical Reagent Co. Ltd.); acetic acid (analytically pure, Shanghai Lingfeng Chemical Reagent Co. Ltd.).

Apparatuses and Instruments

Mini-type multi-functional experiment machine (Chongqing Jinggong Pharmaceutical machine Co. Ltd.); single-punch tablet press (Shanghai Tianfan Pharmaceutical machinery factory); spray dryer (BUCHI); moisture determination meter (Sartorius Co. Ltd., Beijing); intelligent dissolution testing meter (Tianda Tianfa Co. Ltd.); climatic chamber, type 720 (BINDER); BT224S electronic balance (Sartorius Co. Ltd., Beijing); OHHARA lab type coating pan; Agilent 1200 HPLC (Agilent Technology, Co. Ltd.); FE20 type pH meter (METTLER TOLEDO Co. Ltd: Phenomenex Luna C18 100A (250×4.6 mm, 5 μm, Phenomenex Co. Ltd., US); Agilent Eclipse XDB-C18 (150×4.6 mm, 5 μm, Agilent Technology, Co. Ltd., US).

Experimental Examples (1) In-Vitro Test

TABLE 1

The cumulative dissolution release of isoniazid in the isoniazid coated tablet with coated core (Example 1) in aqueous media

| Tablet No. | Weight gain of film, % | The indicated cumulative dissolution (%) | | | The time when coating film began to collapse (') | The time of complete disintegration (') |
|---|---|---|---|---|---|---|
| | | 30 min | 45 min | 60 min | | |
| 4 | 8.2 | 86.12 | 98.91 | 96.81 | 29 | 31 |
| 20 | 8.4 | not sampled | 100.19 | 99.98 | 34 | 35 |
| 26 | 8.2 | not sampled | 97.82 | 98.01 | 32 | 34 |

Note:
According to the experimental experience, when the coating film of the tablet was not broken, the release of isoniazid is relatively small, i.e. less than 10%. Therefore, samples of Tablet No. 20 and 26 were not sampled and measured.

As shown in Table 1, the breaking time of the inner core coating film essentially may be within the required controlled time, i.e. 30 to 60 minutes. After coating film was broken, the drugs could be completely released in a short time.

TABLE 2

The cumulative dissolution release of isoniazid in the isoniazid coated tablet with coated core (Example 2) in aqueous media

| Tablet No. | Weight gain of film, % | The indicated cumulative dissolution (%) | | | | The time when coating film begins to collapse (') | The time of complete disintegration (') |
|---|---|---|---|---|---|---|---|
| | | 30 min | 60 min | 70 min | 84 min | | |
| 1 | 10.5 | 1.56 | 0.98 | 94.66 | not sampled | 60 | 68 |
| 3 | 8.6 | 1.05 | 98.23 | not sampled | not sampled | 48 | 54 |
| 4 | 8.0 | 1.44 | 49.99 | 102.87 | not sampled | 56 | 65 |
| 20 | 8.4 | 1.71 | 99.13 | not sampled | not sampled | 53 | 56 |
| 35 | 9.00 | 1.46 | 10.10 | 75.65 | 97.91 | 60 | 84 |
| 41 | 6.9 | 1.19 | 94.88 | not sampled | not sampled | 36 | 39 |

As shown in Table 2, the coating films in the central layer of the formulations each broke within 30 to 60 minutes. Within 30 minutes, the release of isoniazid is not more than 2%, which is much lower than the 10% standard in the optimized regime for quality control. Within 90 minutes, the drug is essentially completely released.

TABLE 3

The cumulative dissolution release of TB4 coated tablet with coated core (Example 2) (dissolution media: PBS 6.8 buffer, 900 ml)

| Ingredient | 30 min | 45 min | 60 min |
|---|---|---|---|
| $Q_{indicated}$% (H) | 1.55 | 3.01 | 96.32 |
| $Q_{indicated}$% (R) | 80.35 | 95.01 | 94.26 |
| $Q_{indicated}$% (Z) | 85.99 | 95.93 | 97.60 |
| $Q_{indicated}$% (E) | 88.85 | 97.31 | 99.50 |

From the data in Table 3, it can been seen that the release of isoniazid can achieve the standard required for control, i.e. less than 15% released within 30 minutes, and more than 80% released within 90 minutes.

TABLE 4

The cumulative dissolution release of TB4 three-layer coated tablet (Example 5) (dissolution media: PBS 6.8 buffer, 900 ml)

| Ingredient | 30 min | 45 min | 60 min | 90 min |
|---|---|---|---|---|
| $Q_{indicated}$% (H) | 2.51 | 5.07 | 54.80 | 98.17 |
| $Q_{indicated}$% (R) | 80.10 | 97.55 | 97.51 | 96.88 |
| $Q_{indicated}$% (Z) | 2.85 | 6.13 | 60.08 | 100.10 |
| $Q_{indicated}$% (E) | 51.32 | 84.46 | 98.31 | 100.99 |

From the data in Table 3, it can be seen that the release-controlled film and the ethambutol hydrochloride layer were great for the controlling of the delayed-release of isoniazid.

TABLE 5

Summary of the cumulative dissolution release of rifampicin in solid dispersion in different ratios of rifampicin:HPMCAS (w:w) (Example 12)

| R:HPMCAS | Cumulative dissolution $Q_{indicated}$% in pH 1.2 | | | Cumulative dissolution $Q_{indicated}$% in pH 6.8 | | Dissolution condition |
|---|---|---|---|---|---|---|
| | 30 min | 45 min | 60 min | 30 min | 60 min | |
| rifampicin bulk drug | 62.07 | not sampled | 62.66 | 27.77 | 46.45 | ① |
| 3/1 | 30.84 | / | 25.62 | 89.07 | 85.44 | ① |
| 2/1 | not sampled | 10.06 | not sampled | 90.11 | 88.9 | ② |
| 1/1 | 0.93 | not sampled | 0.61 | 80.58 | 90.13 | ① |
| 1/2 | 0.84 | not sampled | 0.83 | 73.89 | 89.42 | ① |
| 1/3 | 0 | not sampled | 0 | 87.05 | 89.99 | ① |

Note:
1) The dissolution condition ① is that acid and base (900 ml each) were not contained in the same cup, and it was independently conducted by paddle method in 100 rpm at 37.0° C. The dissolution condition ② is that acid and base were contained in the same cup. In other words, 750 ml acidic substance (0.1 mol/l hydrochloric acid) is firstly added. Taking sample and adding solution after it was dissoluted for 45 min, while 250 ml 0.2 mol/l sodium phosphate solution was added, and 4.5 ml 2 mol/l sodium hydroxide was added to adjust the solution pH to 6.8 ± 0.05 as the basic media. It was conducted by paddle method in 100 rpm at 37.0° C.

As shown in Table 5, the experiment result indicates that according to the present invention, it has better solubilizing effect for rifampicin by preparing rifampicin to solid dispersions (rifampicin:HPMCAS is 3:1 to 1:3). However, when rifampicin:HPMCAS is 3:1, the release of rifampicin in the acidic stomach condition was out of the control range, and thus such a ratio was not selected for preparation. As can be seen in the table, it is most suitable to select the weight ratio of rifampicin:HPMCAS in 1:1, since it was solubilized, and the release of rifampicin in acid can be controlled, the amount used was also relatively small.

TABLE 6

The measurement result of the release degree of rifampicin in the rifampicin solid dispersions (Example 7, 8, 9, 12, rifampicin:HPMCAS = 1:1) prepared by different preparation methods

| Preparation methods | Example | Cumulative dissolution $Q_{indicated}$ % in pH 1.2 | | Cumulative dissolution $Q_{indicated}$ % in pH 6.8 | |
|---|---|---|---|---|---|
| | | 30 min | 60 min | 30 min | 60 min |
| Rifampicin bulk drug | / | 62.07 | 62.66 | 27.77 | 46.45 |
| Hot melting method | 7 | 3.45 | not sampled | 82.07 | 88.63 |
| Spray drying method | 8 | 7.98 | not sampled | 100.59 | 89.64 |
| One step granulating method | 9 | 1.96 | 7.97 | 98.19 | 97.76 |
| Spontaneous evaporation method | 12 | 0.93 | 0.61 | 80.58 | 90.13 |

The data in Table 6 show that the preparation methods have no significant solubilizing effect on rifampicin.

TABLE 7

The measurement result of related substances in rifampicin solid dispersions (rifampicin:HPMCAS = 1:1) prepared by different preparation method on day 0

| Preparation | Example | Total impurity % |
|---|---|---|
| rifampicin bulk drug, batch No. 0811011 | / | 4.43 |
| Hot melting method | 7 | 5.92 |
| Spray drying method | 8 | 5.01 |
| Spontaneous evaporation method | 12 | 4.87 |

Note:
1) See FIGS. 1 to 4 for the chromatograms. Peak 2 in the figures is the rifampicin peak.
2) The instrument and chromatographic condition: Waters e2695-2998 HPLC chromatograph, Phenmenex luna C18 (250 × 4.6 mm, 5 μm) column; flow rate was 1.0 ml/min, measuring wavelength was 238 nm, mobile phase: phase A = pbs 6.8/acetonitrile(96/4), phase B = pbs 6.8/acetonitrile (50/50), phase A:phase B = 25:75.

As shown in Table 7, the rifampicin stability order of the three preparation method for solid dispersions is spontaneous evaporation method>spray drying method>hot melting method. Combined with the industrialized character for production, spray drying method is preferred.

TABLE 8

The measurement of related substances in the 6-month accelerated experiment (40° C., 75% RH) of the inventive coated tablet with coated core (Example 2) and the commercially available imported product

| Day | Inventive coated tablet with coated core | | | Imported coated tablet with coated core | | |
|---|---|---|---|---|---|---|
| | $Q_{indicated}$ % (R) | $Q_{indicated}$ % (H) | $Q_{indicated}$ % (impurities) | $Q_{indicated}$ % (R) | $Q_{indicated}$ % (H) | $Q_{indicated}$ % (impurities) |
| 0 | 98.03 | 107.48 | 3.61 | 99.70 | 109.47 | 6.98 |
| 15 | 95.26 | 106.14 | 4.33 | 101.05 | 105.47 | 6.71 |
| 30 | 96.33 | 104.82 | 4.68 | 97.25 | 108.06 | 6.48 |
| 90 | 95.17 | 106.68 | 5.81 | 96.13 | 107.76 | 8.20 |
| 180 | 93.09 | 103.04 | 5.05 | 87.18 | 108.16 | 12.39 |

Note:
1) the imported four-ingredient compound coated tablet with coated core is produced by Panacea Biotec Ltd from India (batch No: 9988512). See FIGS. 5 to 6 for the chromatograms, in which peak 1 is pyrazinamide, and peak 2 is rifampicin.
2) The instrument and chromatographic condition: Agilent 1200 HPLC chromatograph, Phenmenex luna C18 (250 × 4.6 mm, 5 μm) column; measuring wavelength was 238 nm, flow rate was 1.0 ml/min, mobile phase: phase A = pbs 6.8/acetonitrile (96/4), phase B = pbs 6.8/acetonitrile (40/60), and the gradient is as below:

| Time (min) | Phase A (%) | Phase B (%) |
|---|---|---|
| 0 | 100 | 0 |
| 10 | 100 | 0 |
| 15 | 65 | 35 |
| 50 | 65 | 35 |
| 56 | 100 | 0 |
| 60 | 100 | 0 |

The stability investigation result in Table 8 indicates that the inventive product is more stable than the imported commercially available product. Therefore, the present invention facilitates to improve the stability of the four-ingredient combined anti-tubercular formulation.

TABLE 9

The measurement of related substances in the inventive product (Example 2) for 12-month stability (25° C., 60% RH)

| T (month) | $Q_{indicated}$ % (R) | $Q_{indicated}$ % (H) | $Q_{indicated}$% (total impurities) |
|---|---|---|---|
| 0 | 98.03 | 107.48 | 3.61 |
| 3 | 97.33 | 106.25 | 4.64 |
| 6 | 97.65 | 106.12 | 4.17 |
| 12 | 102.31 | 106.63 | 6.01 |

Note:
1) See FIG. 7 for the chromatogram, in which peak 1 is pyrazinamide, and peak 2 is rifampicin.
2) The instrument and chromatographic condition: Waters e2695-2998 HPLC chromatograph, Phenmenex luna C18 (250 × 4.6 mm, 5 μm) column; flow rate was 1.0 ml/min, measuring wavelength was 238 nm, mobile phase: phase A = pbs 6.8/acetonitrile (96/4), phase B = pbs 6.8/acetonitrile (50/50), and the gradient is as below:

| Time (min) | Phase A (%) | Phase B (%) |
|---|---|---|
| 0 | 95 | 5 |
| 7 | 95 | 5 |
| 14 | 80 | 20 |
| 40 | 80 | 20 |
| 41 | 95 | 5 |
| 50 | 95 | 5 |

As shown in Table 9, the stability investigation result for a 12-month long term indicates that when left under normal temperature, the impurities due to rifampicin and isoniazid increased in the inventive formulations in the investigation period, but the formulation is still relatively stable.

(2) Beagle In-Vivo Experiment

The Administration Procedure of Single Rifampicin Group:

12 beagles were randomly divided into groups A and B. Each was fed at 8 a.m., and administrated after 0.5 h. Group A were administrated with one tablet of the inventive rifampicin tablet (150 mg, corresponding to 10 mg/kg, rifampicin firstly formed to enteric solid dispersions by spray drying, and then compressed with other adjuvants to produce a coated sample (i.e. sample of Example 11). Group B were administrated with one pill of the rifamipicin capsule produced by Shenyang Hongqi Pharmaceutical Co. Ltd. (150 mg, batch No. 0907011).

The Rifampicin+Isoniazid Combination Administration Procedure

Two weeks after the end of the above experiment, each of groups A and B was fed, and administrated after 0.5 h. Group A were administrated with one tablet of the inventive rifampicin tablet (150 mg, corresponding to 10 mg/kg, the sample is the same as the single administration sample) and one tablet of the isoniazid produced by Shenyang Hongqi Pharmaceutical Co. Ltd. (75 mg/pill, produced by grinding the tablet containing 0.3 g/tablet of batch No. 0907011 and canning). Group B were administrated with one pill of the rifamipicin capsule (150 mg, batch No. 0907011) and one pill of isoniazid (same as group A) produced by Shenyang Hongqi Pharmaceutical Co. Ltd.

TABLE 10

The pharmacokinetics parameters of isoniazid after oral administrating beagles with the inventive (sample of Example 11) and commercially available rifampicin combination formulations (using non-compartment model analysis)

| PK parameters* | Inventive rifampicin + commercially available isoniazid | | commercially available rifampicin + commercially available isoniazid | |
|---|---|---|---|---|
| | Mean | SD | Mean | SD |
| Cmax (μg/L) | 6680.71 | 1574.32 | 4353.66 | 1170.28 |
| Tmax (hr) | 1.00 | 0.46 | 1.45 | 0.83 |
| AUC0-24 h (μg · hr/L) | 27636.25 | 9121.94 | 21616.85 | 3949.48 |
| AUC0-∞ h (μg · hr/L) | 29345.96 | 10307.13 | 23056.16 | 4141.09 |
| T½ (hr) | 2.75 | 0.53 | 2.71 | 0.63 |
| MRT (hr) | 4.33 | 0.49 | 4.75 | 0.85 |

*Cmax: maximum concentration; Tmax: time of reaching the maximum; AUC (0→t h): areas under concentration-time curve (from 0 to t h); AUC (0-∞ h): areas under concentration-time curve (from 0 to ∞ h); T½: elimination half-life; MRT: mean retention time.

TABLE 11

The bioavailability of oral administration of rifampicin to beagles

| The relative bioavailability 1(%) | 152.01 |
|---|---|
| The relative bioavailability 2(%) | 123.68 |

Note:
The relative bioavailability 1 (%) = the mean AUC 0-12 of the inventive single rifampicin tablet/the mean AUC 0-12 of commercially available single rifampicin capsule × 100%;
The relative bioavailability 2 (%) = the mean AUC 0-12 of the inventive rifampicin compound drug tablet/the mean AUC 0-12 of commercially available rifampicin compound drug capsule × 100%.

From the data of AUC 0-24 h and AUC 0-∞ h in Table 10 and Table 11, it can be seen that after rifampicin is produced to solid dispersion, its bioavailability is significantly increased.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A compound oral core-coated solid formulation, in the form of a coated tablet with coated core, comprising rifampicin, isoniazid, pyrazinamide and ethambutol hydrochloride as active ingredients,
   in which the inner core comprises isoniazid or rifampicin, and is coated with a non-pH dependent water soluble isolating film, and the rifampicin is in the form of solid dispersion in which the rifampicin is dispersed in an enteric solid carrier, and the weight ratio range of the rifampicin to the enteric solid carrier is from 2:1 to 1:3, and said enteric solid carrier is hydroxypropyl methyl cellulose acetate succinate (HPMCAS); and
   the outer layer of the core-coated solid formulation is coated with a non-pH dependent water soluble coating film which serves as a barrier to both moisture and light.

2. The compound oral core-coated solid formulation according to claim 1,
   wherein after administration, no more than 15% of rifampicin of the indicated percentage contents is released within 30 minutes in the acidic condition of stomach, and more than 80% of rifampicin of the indicated percentage contents is released within 45 minutes in the intestinal pH condition.

3. The compound oral coating solid formulation according to claim 1, wherein the non-pH dependent water soluble isolating film is formed by one or more materials selected from the group consisting of hydroxypropyl methylcellulose (HPMC), polyvinyl alcohol-polyethylene glycol graft copolymer and Opadry II.

4. The compound oral core-coated solid formulation according to 1, wherein said non-pH dependent water soluble coating film which serves as a barrier to both moisture and light is formed by one selected from the group consisting of polyvinyl alcohol-polyethylene glycol graft copolymer, hydroxypropyl methyl cellulose (HPMC), a combination of titanium dioxide and talc powder, and Opadry II containing a combination of hydroxypropyl methylcellulose (HPMC), titanium dioxide and talc powder.

5. The compound oral core-coated solid formulation according to claim 1, wherein after administration, no more than 15% of the indicated percentage contents of at least one of the active ingredients of rifampicin and isoniazid is released within 30 minutes.

6. The compound oral core-coated solid formulation according to claim 1, further comprising other pharmaceutical carriers selected from the group consisting of: a filler, a binder, a lubricating agent, a glidant, and a disintegrant.

7. The compound oral core-coated solid formulation according to claim 1,
wherein after administration, no more than 10% of rifampicin of the indicated percentage contents is released within 30 minutes in the acidic condition of the stomach, and
more than 85% of rifampicin of the indicated percentage contents is released within 45 minutes in the intestinal pH condition.

8. The compound oral core-coated solid formulation of claim 1, wherein the weight ratio of the rifampicin to the enteric solid carrier is 1:1.

* * * * *